United States Patent [19]
Kohayakawa

[11] Patent Number: 5,585,872
[45] Date of Patent: Dec. 17, 1996

[54] OPHTHALMIC MEASURING APPARATUS FOR DETERMINING THE SHAPE OF THE CORNEA OF AN EYE

[75] Inventor: Yoshimi Kohayakawa, Yokohama, Japan

[73] Assignee: Canon Kabushiki Kaisha, Tokyo, Japan

[21] Appl. No.: 251,967

[22] Filed: Jun. 1, 1994

[30] Foreign Application Priority Data

Jun. 3, 1993 [JP] Japan ................................. 5-160420

[51] Int. Cl.$^6$ ........................... A61B 3/10; A61B 3/14
[52] U.S. Cl. ...................... 351/212; 351/210; 351/221; 351/247
[58] Field of Search ...................... 351/200, 205, 351/208, 210, 211, 221, 212, 247; 356/138

[56] References Cited

U.S. PATENT DOCUMENTS

| | | | |
|---|---|---|---|
| 4,609,287 | 9/1986 | Kohayakawa | 356/124 |
| 4,697,895 | 10/1987 | Sekiguchi et al. | 351/243 |
| 4,704,012 | 11/1987 | Kohayakawa et al. | 350/516 |
| 4,820,037 | 4/1989 | Kohayakawa et al. | 351/211 |
| 4,825,873 | 5/1989 | Kohayakawa | 128/648 |
| 4,826,315 | 5/1989 | Kohayakawa | 356/125 |
| 4,830,483 | 5/1989 | Kohayakawa et al. | 351/221 |
| 4,954,843 | 9/1990 | Oka et al. | 355/210 |
| 5,031,623 | 7/1991 | Kohayakawa et al. | 128/648 |
| 5,033,841 | 7/1991 | Nishio et al. | 351/212 |
| 5,037,194 | 8/1991 | Kohayakawa et al. | 351/224 |
| 5,042,940 | 8/1991 | Iwamoto | 351/208 |
| 5,144,346 | 9/1992 | Nakamura et al. | 351/208 |
| 5,231,430 | 7/1993 | Kohayakawa et al. | 351/243 |
| 5,231,460 | 7/1993 | Kohayakawa et al. | 356/125 |
| 5,237,351 | 8/1993 | Kohayakawa et al. | 351/243 |
| 5,249,003 | 9/1993 | Kohayakawa | 351/211 |
| 5,280,313 | 1/1994 | Kohayakawa | 351/211 |
| 5,325,134 | 6/1994 | Kohayakawa | 351/212 |

FOREIGN PATENT DOCUMENTS

| | | |
|---|---|---|
| 191831 | 4/1989 | Japan . |
| 2220626 | 9/1990 | Japan . |
| 2129963 | 5/1984 | United Kingdom ............ 351/211 |

*Primary Examiner*—William L. Sikes
*Assistant Examiner*—Huy Mai
*Attorney, Agent, or Firm*—Fitzpatrick, Cella, Harper & Scinto

[57] ABSTRACT

An ophthalmic measuring apparatus has an optical system for measurement, a light source unit for measurement, an image pickup element for picking up the cornea reflection image of the light source by an eye to be examined through the optical system for measurement, a signal processing unit for effecting cornea shape measurement from the image pickup data of the cornea reflection image obtained by the image pickup element, and a control unit for automatically causing the signal processing unit to execute measurement on the basis of the information of the position, on the image pickup element, of the cornea reflection image obtained by the image pickup element and/or the focusing information of the cornea reflection image.

23 Claims, 2 Drawing Sheets

FIG. 4
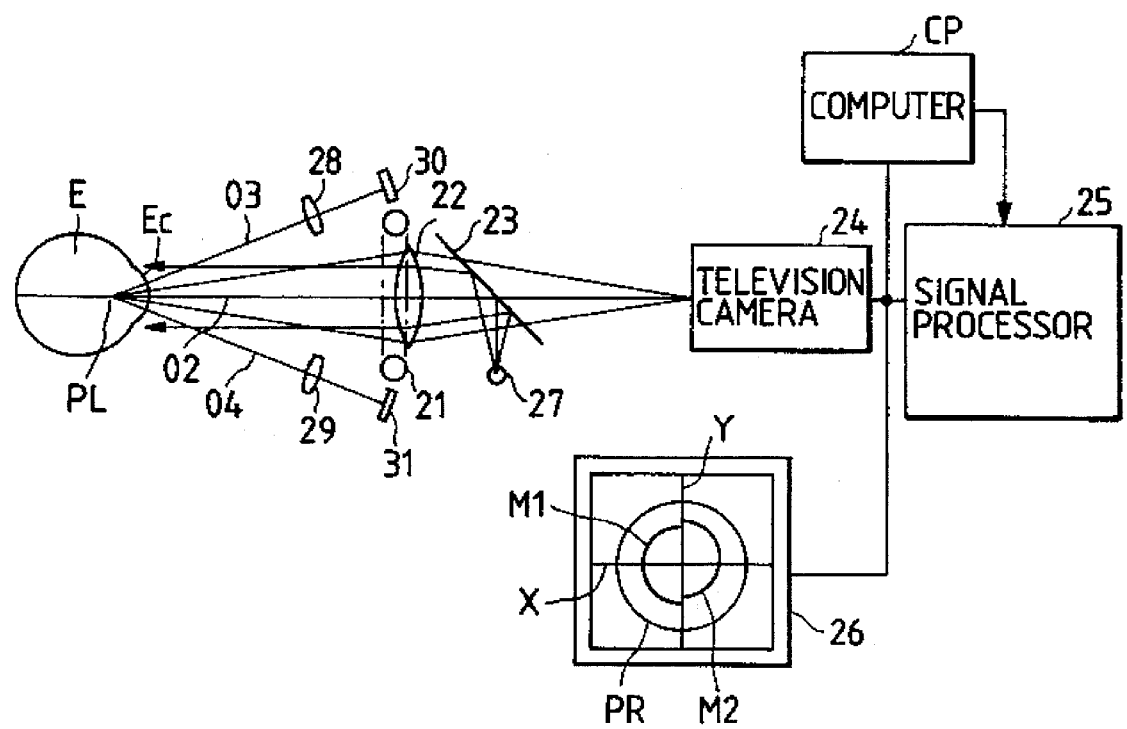
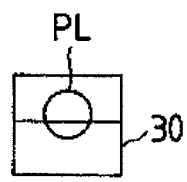
FIG. 5A
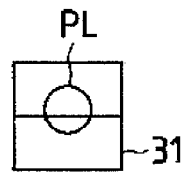
FIG. 5B

OPHTHALMIC MEASURING APPARATUS FOR DETERMINING THE SHAPE OF THE CORNEA OF AN EYE

BACKGROUND OF THE INVENTION

1. Field of the Invention

This invention relates to an ophthalmic measuring apparatus for use in ophthalmic clinics or the like.

2. Related Background Art

A cornea shape measuring apparatus according to the present invention is such that a beam of light from a light source is imaged on the cornea, this image of the light source is observed through a monitor or a lens, the focus and image position of this image of the light source are adjusted to thereby effect alignment, and a measurement button is depressed to start the measurement of the cornea shape.

To accomplish highly accurate cornea shape measurement, it is necessary to effect the alignment of the apparatus accurately. Heretofore, however, the judgment of the termination of the alignment of the apparatus has depended on visually recognizing the image of the light source and therefore, such judgment differs for each time of measurement due to differences between individual examiners or even by the same examiner and thus, the measured value becomes unstable. Also, to effect measurement, there is the cumbersomeness that the measurement starting button must be newly depressed, and skill is required for the operation of the apparatus.

Japanese Laid-Open Patent Application No. 1-91831 discloses a cornea shape measuring apparatus in which when cornea shape measurement is to be effected by the use of the cornea reflection images of four light sources for measurement around an optical axis, the setting of the quantity of light is automatically effected when it is recognized that the number of the cornea reflection images has reached a predetermined number, whereafter the starting of the measurement is confirmed.

Also, Japanese Laid-Open Patent Application No. 2-220626 discloses a construction in which when cornea shape measurement is to be effected by the use of the cornea reflection image of a light source for measurement, an alignment state is detected from the quantity of the cornea reflected light and the cornea reflection image of the light source for measurement is introduced when the quantity of said light is a predetermined value or greater.

SUMMARY OF THE INVENTION

It is a first object of the present invention to provide an ophthalmic measuring apparatus in which it is confirmed that the focus or position of a cornea reflection image actually used in the measurement of the cornea is good and then cornea measurement is effected and thus, which is simple to operate and can accomplish accurate measurement.

It is a second object of the present invention to provide an ophthalmic measuring apparatus in which cornea measurement is automatically effected by the utilization of a cornea reflection image displayed on display means for observation and thus, which is simple in construction and operation and can accomplish accurate measurement.

Other objects of the present invention will become apparent from the following detailed description of some embodiments of the invention.

BRIEF DESCRIPTION OF THE DRAWINGS

FIG. 4 shows the construction of a second embodiment of the present invention.

FIGS. 5A and 5B are illustrations of light source images received by photoelectric sensors.

DESCRIPTION OF THE PREFERRED EMBODIMENTS

Figure 1:
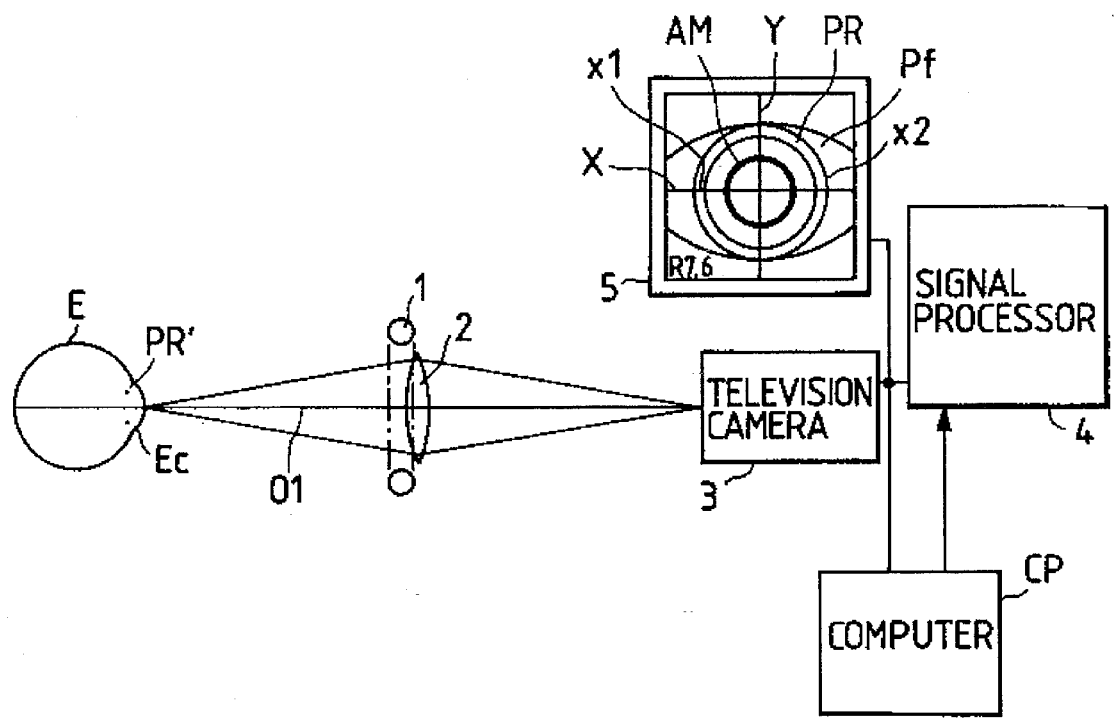
FIG. 1 shows the construction of a first embodiment of the present invention.

The present invention will hereinafter be described in detail with respect to some embodiments thereof shown in the drawings.

Referring to FIG. 1 which shows the construction of a first embodiment of the present invention, a ring light source 1, a lens 2 and a television camera 3 are disposed on an optical path 01 in succession from an eye E to be examined. One of the two outputs of the television camera 3 is connected to a television monitor 5 through a signal processor 4 comprising a frame memory or the like, and the other output of the television camera 3 is directly connected to the television monitor 5. Further, a computer CP is connected to the television camera 3.

A beam of reflected light from the front eye part of the eye E to be examined by a separate illuminating light source, not shown, is imaged as a front eye part image Pf on the television camera 3 through the lens 2, and the front eye part image Pf is displayed on the television monitor 5. The beam of light from the ring light source 1 is again imaged as a ring-shaped virtual image PR' on the cornea Ec of the eye E to be examined, and this beam of reflected light is image as a ring imaged PR on the television camera 3 through the lens 2, and the ring image PR is displayed on the television monitor 5 with the front eye part image Pf. Further, an annular alignment mark AM having a point of intersection between the optical axis 01 and the image pickup element of the television camera 3 as the center of symmetry and segments X and Y are displayed on the television monitor 5 by the output of the computer.

The examiner effects alignment while observing the television monitor 5. He first effects the adjustment of the apparatus in the direction of the optical axis 01, effects the focusing of the ring image PR, and then brings the ring image PR into coincidence with the alignment mark AM. During the alignment, the components of the video signal of the television camera 3 in the directions of the segments X and Y are introduced into a computer CP and the monitoring of the alignment is effected.

Figure 2:
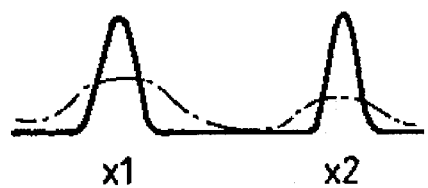
FIG. 2 is a graph showing the distribution of the quantity of light of the light reception signal of a television camera.

FIG. 2 shows the light reception signal in the direction of the segment X on the image pickup element of the television camera 3 which is introduced into the computer CP, and this signal has two peaks near the points of intersection x1 and x2 between the segment X and the ring image PR. In a state in which the ring image PR is out of focus, the light reception signal has gentle peaks of small intensity as indicated by a dot-and-dash line, and in a state in which the ring image PR is in focus, the light reception signal has sharp peaks of great intensity as indicated by a solid line.

The computer CP analyzes the shape of the light reception signal and determines whether the ring image PR is in focus.

Also, the positions of the points of intersection x1 and x2 between the ring image PR and the segment X on the image pickup element of the television camera 3 are determined from the peak positions of the light reception signal. A similar analysis is done about the component of the light reception signal in the direction of the segment Y, and the two points of intersection between the ring image PR and the segment Y on the image pickup element of the television camera 3 are determined.

When after the completion of the focusing, the ring image PR is brought to be concentric with the alignment mark AM, the four points of intersection between the ring image PR and the segments X and Y become center-symmetrical with respect to the optical axis 01, and the computer CP determines that the alignment including the above-described focusing and alignment in X and Y directions has been completed. Further, the computer CP analyzes the signal intensities at the four points of intersection between the ring image PR and the segments X and Y, and if these intensities are uniform, the computer confirms that the light is not eclipsed by the eyelid or the like and measurement is possible. Check-up only in the vertical direction will suffice if only the eyelid should be checked up, but to detect a disturbance or the like of the tear liquid layer, it is preferable to add an analysis in the horizontal direction.

In the actual measurement, the determination as to the completion of the above-described alignment and the determination as to whether measurement is possible or impossible are repetitively effected in the computer CP during the alignment. When the alignment conditions become satisfied, the video signals of the television camera 3 are automatically outputted to the frame memory of the signal processor 4, that is, the measurement is automatically started. Then the shape of the ring image PR is analyzed by the signal processor 4, whereby the radius of curvature of the cornea including the astigmatism of the cornea is calculated, and it is displayed on the left lower portion of the screen of the television monitor 5.

If here, besides the components of the light reception signal in X and Y directions, components in more directions are introduced into the computer CP, more accurate monitoring of alignment or the detection of eyelashes by a defect in the ring image or the detection of measurement being impossible could be possible. Also, it will be convenient if the apparatus produces a sound or a display is effected on the television monitor 5 when the video signals of the television camera 3 are introduced into the signal processor 4 for the measurement.

Figure 3:
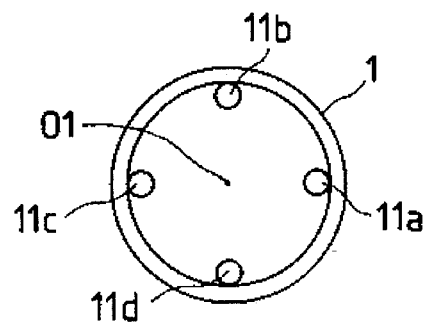
FIG. 3 is a front view of a ring light source and point light sources.

In this embodiment, a single ring light source 1 is used in common for alignment and cornea shape measurement, but as shown in FIG. 3, four point light sources 11a–11d can be additionally provided inside the ring light source 1. When alignment is to be effected, the ring light source 1 is turned on, and when measurement is to be effected, the point light sources 11a–11d are turned on.

The beams of light from the point light sources 11a–11d are formed as a virtual image PR' comprising four small circles on the cornea Ec of the eye E to be examined, and this beam of reflected light is formed as spot images comprising four small circles on the television camera 3 through the lens 2. When the alignment conditions are all satisfied as described above, the light reception signal of the television camera 3 is automatically taken into the signal processor 4, in which the radius of curvature of the cornea is calculated from the positions of the four spot images.

Conversely, when alignment is to be effected, the point light sources 11a–11d may be turned on, and when cornea shape measurement is to be effected, the ring light source 1 may be turned on.

Also, in this embodiment, the image pickup element of a single television camera 3 is used in common for alignment and cornea shape measurement, but alternatively, a plurality of one-dimensional CCDs may be separately disposed for cornea shape measurement. In such case, when the alignment is to be effected, the light reception signal of the one-dimensional CCD or the image pickup element of the television camera 3 can be introduced into the computer.

Further, regarding the alignment in the direction of the optical axis and in a direction perpendicular to the optical axis, a point light source may be separately provided on the optical axis 01 and the blur and position of the cornea reflection image may be analyzed by the video signal of the cornea reflection image thereof.

Referring now to FIG. 4 which shows the construction of a second embodiment of the present invention, a ring light source 21, a lens 22, a dichroic mirror 23 and a television camera 24 are disposed on an optical axis 02 in succession from an eye E to be examined. One of the two outputs of the television camera 24 is connected to a television monitor 26 through a signal processor 25, and the other output of the television camera 24 is directly connected to the television monitor 26. Also, a light source 27 is disposed in the direction of extension of the optical axis 02 and lenses 28, 29 and two element photoelectric sensors 30, 31 are disposed on two optical paths 03 and 04 inclined with respect to the optical axis 02, in succession from the eye E to be examined, and a pattern generating circuit, not shown, for forming alignment marks M1 and M2 on the monitor on the basis of the outputs of the photoelectric sensors 30 and 31 is connected to the outputs of the photoelectric sensors 30 and 31. Also, the components of the video signal in the directions of segments X and Y are introduced into the computer CP as previously described and the monitoring of alignment is effected.

The beam of light from the ring light source 21 is formed as a ring image PR on the cornea Ec of the eye E to be examined, and the beam of reflected light here passes the dichroic mirror 23 and is formed as a ring image PR on the television camera 24, and this ring image is displayed on the television monitor 26.

The beam of light from the light source 27 is reflected by the dichroic mirror 23, is collimated by the lens 22 and is formed as a light source image PL on the cornea Ec of the eye E to be examined. The beam of reflected light on the cornea Ec by this beam of light passes through the lenses 28 and 29, and is formed as small circular light source images PL on the photoelectric sensors 30 and 31, respectively, as shown in FIGS. 5A and 5B. The light reception signals of the two element photoelectric sensors 30 and 31 are analyzed by the signal processor 25 and are displayed as semicircular alignment marks M1 and M2, respectively, on the television monitor 26 with the ring image PR.

The examiner first effects alignment in the direction of the optical axis 02 while observing the television monitor 26. When the apparatus is at the right working distance, the quantities of light of the light source images PL on the two elements of the photoelectric sensors 30 and 31 become the same and the two alignment marks M1 and M2 form an annular shape having the optical axis 02 as the center of symmetry. When the position of the apparatus deviates from the proper working distance, the alignment marks M1 and M2 will vertically deviate from each other and will not form an annular shape. The examiner adjusts the apparatus in the direction of the optical axis 02 so that the alignment marks M1 and M2 may become annular. The examiner then adjusts the apparatus in a direction perpendicular to the optical axis 02, brings the ring image PR into coincidence with the alignment marks M1 and M2 which have become annular, and effects alignment in the direction perpendicular to the optical axis 02.

During the alignment, the light reception signal of the cornea reflection image PR of the light source 21 of the components in the directions of the segments X and Y centering around the point of intersection between the optical axis 02 and the image pickup element of the television monitor 26 are consecutively taken into the computer and the monitoring of whether the alignment state and the detection of measurement are impossible are effected. The signal processing in the computer is similar to that in the first embodiment. When the computer CP determines that the four points of intersection between the ring image PR and the segments X, Y are center-symmetrical and the distribution of the quantity of light at the points of intersection is uniform, the video signals of the ring image PR from the television camera 24 are immediately outputted to the signal processor 25 and the radius of curvature of the cornea is calculated. In the above mentioned judgement of alignment the signal from the sensors 30 and 31 can be used in addition.

Again in this embodiment, the point light sources 11a–11d shown in FIG. 3 may be separately provided for alignment.

As described above, the cornea shape measuring apparatus according to the above-described embodiments detects the cornea reflection image of the light source provided around the optical axis, and when it is determined from this detection signal that alignment has been completed and measurement is possible, the apparatus automatically effects cornea shape measurement and therefore can accurately measure the radius of curvature of the cornea at the point in time at which the alignment has been done, and it is unnecessary to perform the operation of depressing a measurement button and thus, any examiner unskilled in operation can effect highly accurate and stable cornea shape measurement.

In the above-described embodiments, it is desirable that the determination of the completion of alignment be done about both of focusing and alignment in X and Y directions, but depending on the apparatus, such determination may be done about only one of them.

What is claimed is:

1. An ophthalmic measuring apparatus comprising:

an optical system used for performing a cornea shape measurement of an eye to be examined;

a light source unit used for performing the cornea shape measurement of the eye to be examined;

a photoelectric device for detecting a first cornea reflection image of said light source unit reflected by an eye to be examined through said optical system and for detecting a second cornea reflection image of light source means arranged inside said light source unit in the event light source means is in said light source unit;

a signal processing unit for analysing said first or second cornea reflection image from data of said cornea reflection image obtained by said photoelectric device and for performing cornea shape measurement of the eye to be examined therefrom; and a control unit for determining based on data from said photoelectric device information on the position of said first or second cornea reflection image on said photoelectric device, focusing information of said first or second cornea reflection image, and information on the uniformity of the quantity of light of said first or second cornea reflection image, and for automatically starting said signal processing unit to execute cornea shape measurement on the basis of at least one of the information on the position of said first or second cornea reflection image on said photoelectric device, the focusing information of said first or second cornea reflection image, and the information on the quantity of light of said first or second cornea reflection image.

2. The apparatus of claim 1, wherein said control unit automatically causes said signal processing unit to execute the cornea shape measurement when it recognizes that the positions of the plurality of portions of said first or second cornea reflection image on said photoelectric device have become symmetrical with respect to the optical axis of said optical system.

3. The apparatus of claim 1, wherein said control unit analyzes the light distribution of said first or second cornea reflection image detected by said photoelectric device and determines the focus of said first or second cornea reflection image, and automatically causes said signal processing unit to execute the cornea shade measurement when it recognizes that the said first or second cornea reflection image is in focus.

4. The apparatus of claim 1, wherein said control unit further automatically causes said signal processing unit to execute the cornea shade measurement on the basis of the uniformity of the quantity of light of said first or second cornea reflection image.

5. The apparatus of claim 1, wherein said light source unit has at least one light source disposed around an optical axis of said optical system for measurement.

6. The apparatus of claim 1, further comprising a monitor for displaying an alignment state of said apparatus and the eye to be examined.

7. The apparatus of claim 6, further comprising optical detecting means for optically detecting an alignment state of said apparatus and the eye to be examined in the direction of an optical axis of said optical system for measurement.

8. The apparatus of claim 7, wherein said monitor mark-displays the alignment state of said apparatus and the eye to be examined on the basis of the detection by said optical detecting means.

9. The apparatus of claim 6, wherein said monitor also displays the result of the measurement by said signal processing unit.

10. The apparatus of claim 1, wherein said control unit first causes to output data collected by said photoelectric device to a frame memory of said signal processing unit on the basis of one of the information of the position on said photoelectric device of said first or second cornea reflection image and defocus information of said first or second cornea reflection image obtained by said photoelectric device.

11. The apparatus of claim 1, wherein said light source unit has a ring-shaped light source.

12. The apparatus of claim 1, further comprising a display unit for displaying that the measurement by said signal processing unit has been effected.

13. The apparatus of claim 12, wherein said display unit displays the result of the measurement as the display of the fact that the measurement has been effected.

14. The apparatus of claim 1, further comprising at least one light source for detecting the distance between the eye and said optical system.

15. The apparatus of claim 14, wherein said light source unit is commonly used for detecting the distance.

16. The apparatus of claim 1, wherein said photoelectric device is an image pickup device.

17. The apparatus of claim 16, further comprising a monitor for displaying the image picked up by said image pickup device and the result of the measurement by said signal processing unit.

18. The apparatus of claim 1, wherein said light source unit has point light sources.

19. An ophthalmic measurement apparatus comprising:

an optical system used for cornea shape measurement of an eye to be examined;

a light source unit;

a light receiving element for receiving light from an eye to be examined illuminated by said light source unit, through said optical system used for cornea shape measurement of the eye to be examined;

a signal processing unit for performing the cornea shade measurement of the eye to be examined from a signal from said light receiving element;

an observation system for the eye to be examined having an image pickup unit for performing the image pickup of the image of the eye to be examined, and a display unit for performing the display of the image of the eye to be examined picked up by said image pickup unit; and a control unit for automatically causing said signal processing unit to execute cornea shape measurement of the eye to be examined on the basis of eye position information obtained from the image of the eye to be examined picked up by said image pickup unit.

20. The apparatus of claim 19, wherein said light receiving element is an image pickup element for use in common with the image pickup unit of said observation system for the eye to be examined.

21. An ophthalmic measuring apparatus comprising;

a light source unit used for a cornea shape measurement of an eye to be examined;

a photoelectric device for detecting the cornea reflection image of said light source unit reflected by the eye to be examined;

a signal processing unit for analyzing said reflection image from the data of said cornea reflection image obtained by said photoelectric device and for performing the cornea shape measurement of the eye to be examined therefrom; and a control unit for determining from data from said photoelectric device, information on the position of the cornea reflection image on said photoelectric device, focusing information of the cornea reflection image, and information on the uniformity of the quantity of light of the cornea reflection image, and for automatically starting said signal processing unit to execute the cornea shape measurement of the eye to be examined on the basis of at least one of the information of the position of the cornea reflection image on said photoelectric device, the focusing information, and information on the uniformity of the quantity of light of the cornea reflection image obtained by said photoelectric device.

22. An ophthalmic measuring apparatus comprising:

an optical system used for a cornea shape measurement of an eye to be examined;

a light source unit used for the cornea shape measurement of the eye to be examined;

a photoelectric device for detecting the cornea reflection image of said light source unit reflected by the eye to be examined through said optical system used for the cornea shape measurement of the eye to be examined and for producing data of the cornea reflection image;

a signal processing unit for analyzing said cornea reflection image from the data of said cornea reflection image obtained by said photoelectric device and for performing the cornea shape measurement of the eye to be examined therefrom; and a detecting unit for detecting information of the position on said photoelectric device, focusing information, and information on the uniformity of the quantity of light, of said cornea reflection image, and for detecting information on the position of a cornea reflection image of light source means arranged in said light source unit on said photoelectric device, focusing information of the cornea reflection image of the light source means, and information on the uniformity of the quantity of light of the cornea reflection image of the light source means, obtained by said photoelectric device in the event said light source unit has light source means arranged therein.

23. An ophthalmic measuring apparatus comprising:

a light source unit used for a cornea shape measurement of an eye to be examined;

a photoelectric device for detecting the cornea reflection image of said light source unit reflected by the eye to be examined and for producing data of the cornea reflection image;

a signal processing unit for analyzing said reflection image from the data of said cornea reflection image obtained by said photoelectric device for the cornea shape measurement of the eye to be examined;

a control unit for automatically starting said signal processing unit to execute the cornea shape measurement of the eye to be examined; and sound producing means for producing a sound when said signal processing unit automatically starts to execute the cornea shape measurement of the eye to be examined.

* * * * *

UNITED STATES PATENT AND TRADEMARK OFFICE
CERTIFICATE OF CORRECTION

PATENT NO. : 5,585,872        Page 1 of 2
DATED      : December 17, 1996
INVENTOR(S): YOSHIMI KOHAYAKAWA, ET AL.

It is certified that error appears in the above-indentified patent and that said Letters Patent is hereby corrected as shown below:

COLUMN 2:

Line 37, "image" should read --imaged--.
    Line 38, "imaged" should read --image--.

COLUMN 3:

Line 44, "is effected" should be deleted.

COLUMN 5:

Line 46, "such" should read --such a--.
    Line 60, "analysing" should read --analyzing--.

COLUMN 6:

Line 7, "the" (second occurrence) should be deleted.
    Line 9, "the" should be deleted.
    Line 11, "the" (first occurrence) should be deleted.
    Line 25, "shade" should read --shape--.
    Line 30, "shade" should read --shape--.
    Line 51, "to output" should read --the output of--.

UNITED STATES PATENT AND TRADEMARK OFFICE
CERTIFICATE OF CORRECTION

PATENT NO. : 5,585,872

DATED : December 17, 1996

INVENTOR(S) : YOSHIMI KOHAYAKAWA, ET AL.

It is certified that error appears in the above-indentified patent and that said Letters Patent is hereby corrected as shown below:

COLUMN 7:

Line 19, "shade" should read --shape--.
    Line 38, "comprising;" should read --comprising:--.

COLUMN 8:

Line 1, "the" (second occurrence), should be deleted.
    Line 3, "the" should be deleted, and "information," should read --information on the cornea reflection image,--.
    Line 23, "of" should read --of at least one of--.
    Line 26, "and" should read --or--.
    Line 27, "on" should read --of at least one of--.
    Line 29, "in" should read --closely to--.

Signed and Sealed this

Third Day of February, 1998

Attest:

BRUCE LEHMAN

Attesting Officer     Commissioner of Patents and Trademarks